(12) United States Patent
Nakamura et al.

(10) Patent No.: US 10,592,758 B2
(45) Date of Patent: Mar. 17, 2020

(54) OCCUPANT MONITORING DEVICE FOR VEHICLE

(71) Applicant: SUBARU CORPORATION, Tokyo (JP)

(72) Inventors: Ryota Nakamura, Tokyo (JP); Masayuki Marubashi, Tokyo (JP); Keita Onishi, Tokyo (JP)

(73) Assignee: SUBARU CORPORATION, Tokyo (JP)

( * ) Notice: Subject to any disclaimer, the term of this patent is extended or adjusted under 35 U.S.C. 154(b) by 0 days.

(21) Appl. No.: 16/207,297

(22) Filed: Dec. 3, 2018

(65) Prior Publication Data

US 2019/0236388 A1 Aug. 1, 2019

(30) Foreign Application Priority Data

Feb. 1, 2018 (JP) ................. 2018-016560

(51) Int. Cl.
*G08B 23/00* (2006.01)
*G06K 9/00* (2006.01)
(Continued)

(52) U.S. Cl.
CPC ............ *G06K 9/00845* (2013.01); *A61B 5/18* (2013.01); *B60K 28/066* (2013.01); *G06K 9/00288* (2013.01); *G08B 21/06* (2013.01)

(58) Field of Classification Search
CPC .... G06K 9/00845; G08B 21/06; G08B 21/02; G08B 21/0407; B60K 28/066; A61B 5/18; B60W 40/08; B60W 2040/0827; B60W 40/09; B60W 2040/0872; B60W 2040/0836; B60W 2540/28; H04N 7/188; H04N 7/183; G06F 16/22; B60R 25/255; B60R 25/1004; B60R 25/25; B60R 25/305
(Continued)

(56) References Cited

U.S. PATENT DOCUMENTS 9,988,055 B1 * 6/2018 O'Flaherty ............. H04W 4/90
2005/0226472 A1 10/2005 Komura
(Continued)

FOREIGN PATENT DOCUMENTS

JP 2004330979 11/2004
JP 2005-301742 A 10/2005
(Continued)

OTHER PUBLICATIONS

Office Action for JP Patent Application No. 2018-016560, dated Jul. 16, 2019, 04 pages of Office Action and 04 pages of English Translation.

*Primary Examiner* — Anh V La
(74) *Attorney, Agent, or Firm* — Chip Law Group

(57) ABSTRACT

An occupant monitoring device which is provided in a vehicle, and monitors one or more occupants riding in the vehicle. The occupant monitoring device includes: a recognizer that recognizes one or more occupants riding in the vehicle; a monitor that monitors the one or more occupants riding in the vehicle according to a result of recognition of the one or more occupants by the recognizer; a start controller that individually starts or stops the recognizer and the monitor. The start controller starts the recognizer in a stopped state of the monitor.

13 Claims, 7 Drawing Sheets

(51) Int. Cl.
*A61B 5/18* (2006.01)
*B60K 28/06* (2006.01)
*G08B 21/06* (2006.01)

(58) Field of Classification Search
USPC .................. 340/576, 575, 573.1, 574, 426.1; 382/115
See application file for complete search history.

(56) References Cited

U.S. PATENT DOCUMENTS

| | | | |
|---|---|---|---|
| 2006/0072792 A1* | 4/2006 | Toda | B60R 25/1004 |
| | | | 382/115 |
| 2008/0215209 A1 | 9/2008 | Ikeda et al. | |
| 2013/0069773 A1* | 3/2013 | Li | B60K 28/02 |
| | | | 340/426.1 |
| 2013/0120574 A1 | 5/2013 | Omi | |
| 2013/0162794 A1* | 6/2013 | Wakiyama | A61B 5/18 |
| | | | 348/77 |
| 2015/0258892 A1 | 9/2015 | Wu | |
| 2015/0294547 A1 | 10/2015 | Ito et al. | |
| 2016/0171319 A1* | 6/2016 | Nagai | G06K 9/00 |
| | | | 382/103 |

FOREIGN PATENT DOCUMENTS

| | | |
|---|---|---|
| JP | 2006-099395 A | 4/2006 |
| JP | 2007-145199 A | 6/2007 |
| JP | 2008-213634 A | 9/2008 |
| JP | 2009-255864 A | 11/2009 |
| JP | 2013103530 | 5/2013 |
| JP | 2013109447 | 6/2013 |
| JP | 2015-115045 A | 6/2015 |
| JP | 2015-214171 A | 12/2015 |
| JP | 2016-167189 A | 9/2016 |

* cited by examiner

FIG. 4

| OCCUPANT MONITORING ~38 | INDIVIDUAL RECOGNITION ~39 | INATTENTIVE DRIVING DETECTION | DROWSY DRIVING DETECTION | INDIVIDUAL RECOGNITION |
|---|---|---|---|---|
| ON | ON | ENABLED | ENABLED | ENABLED |
| ON | OFF | ENABLED | ENABLED | DISABLED |
| OFF | ON | DISABLED | DISABLED | RECOGNITION PROCESSING ONLY (ID IDENTIFICATION FLAG = INDEFINITE) |
| OFF | OFF | DISABLED | DISABLED | DISABLED |

| INDIVIDUAL DATA | FACE DATA | OCCUPANT MONITORING | INDIVIDUAL RECOGNITION | INDIVIDUAL SETTING DATA |
|---|---|---|---|---|
| 001 | ○ | ON | ON | OCCUPANT MONITORING ON, INDIVIDUAL RECOGNITION ON, SETTING DATA (SPEAKER ON, VIBRATION ON, POSITION VALUE) |
| 002 | ◇ | OFF | ON | OCCUPANT MONITORING OFF, INDIVIDUAL RECOGNITION ON, SETTING DATA (SPEAKER ON, VIBRATION OFF, POSITION VALUE) |
| 003 | ▽ | OFF | OFF | OCCUPANT MONITORING OFF, INDIVIDUAL RECOGNITION OFF, SETTING DATA (SPEAKER OFF, VIBRATION OFF, POSITION VALUE) |

OCCUPANT MONITORING DEVICE FOR VEHICLE

CROSS-REFERENCE TO RELATED APPLICATIONS

The present application claims priority from Japanese Patent Application No. 2018-016560 filed on Feb. 1, 2018, the entire contents of which are hereby incorporated by reference.

BACKGROUND

1. Technical Field

The present invention relates to a device that monitors occupants of a vehicle such as an automobile.

2. Related Art

In a vehicle such as an automobile, it may be desirable that an occupant such as a driver riding on the vehicle be monitored (Japanese Unexamined Patent Application Publication Nos. 2013-103530, 2013-109447, and 2004-330979).

An occupant monitoring device recognizes, for instance, an occupant riding on a vehicle, monitors inattentive driving and/or drowsy driving of a driver, and gives warning to the driver.

Thus, attention of the driver is focused on the driving of the vehicle, and improved safety can be expected.

SUMMARY OF THE INVENTION

An aspect of the present invention provides an occupant monitoring device for a vehicle. The occupant monitoring device is mountable in the vehicle and configured to monitor one or more occupants riding in the vehicle. The occupant monitoring device includes: a recognizer configured to recognize one or more occupants riding in the vehicle; a monitor configured to monitor the one or more occupants riding in the vehicle according to a result of recognition of the one or more occupants by the recognizer; and a start controller configured to individually start or stop the recognizer and the monitor. The start controller starts the recognizer with the monitor in a stopped state.

BRIEF DESCRIPTION OF THE DRAWINGS

FIG. 4 is an explanatory table of correspondence relationships between setting values of monitoring start setting data, setting values of recognition start setting data of FIG. 3, and turn on/off states of the occupant monitoring device;

FIG. 5 is an explanatory table for the data structure of the individual database of FIG. 3;

DETAILED DESCRIPTION

In the following, some preferred examples of the technology are described in detail with reference to the accompanying drawings. Note that the following description is directed to illustrative examples of the disclosure and not to be construed as limiting to the technology. Factors including, without limitation, numerical values, dimensions, shapes, materials, components, positions of the components, and how the components are coupled to each other are for purposes of illustration to give an easier understanding of the technology, and are not to be construed as limiting to the technology, unless otherwise specified. Further, elements in the following examples which are not recited in a most-generic independent claim of the disclosure are optional and may be provided on an as-needed basis. The drawings are schematic and are not intended to be drawn to scale. Throughout the specification and the drawings, elements having substantially the same function and configuration are denoted with the same minerals to avoid redundant description. Illustration of elements that are not directly related to the technology is omitted.

Some occupants may think that warning given by an occupant monitoring device is unnecessary or may feel that the warning is annoying.

Thus, it is desirable that start or stop of the occupant monitoring device can be set by an operation of an occupant.

However, even when a turned off occupant monitoring device is turned on, the occupant monitoring device cannot start monitoring each occupant riding in a vehicle unless each occupant is recognized.

When an occupant such as a driver is replaced during travel of a vehicle, a replacing occupant has to wait until the occupant monitoring device finishes recognizing the occupant.

If vehicle travel is resumed before the occupant monitoring device finishes recognizing each occupant, the occupant monitoring device may monitor an occupant different from an actual driver for inattentive driving and/or drowsy driving with the occupant recognized as the driver. It is not preferable that use of the occupant monitoring device be allowed in such a situation.

It is desirable that the occupant monitoring device be preferably turned on or off in a vehicle.

Figure 1:
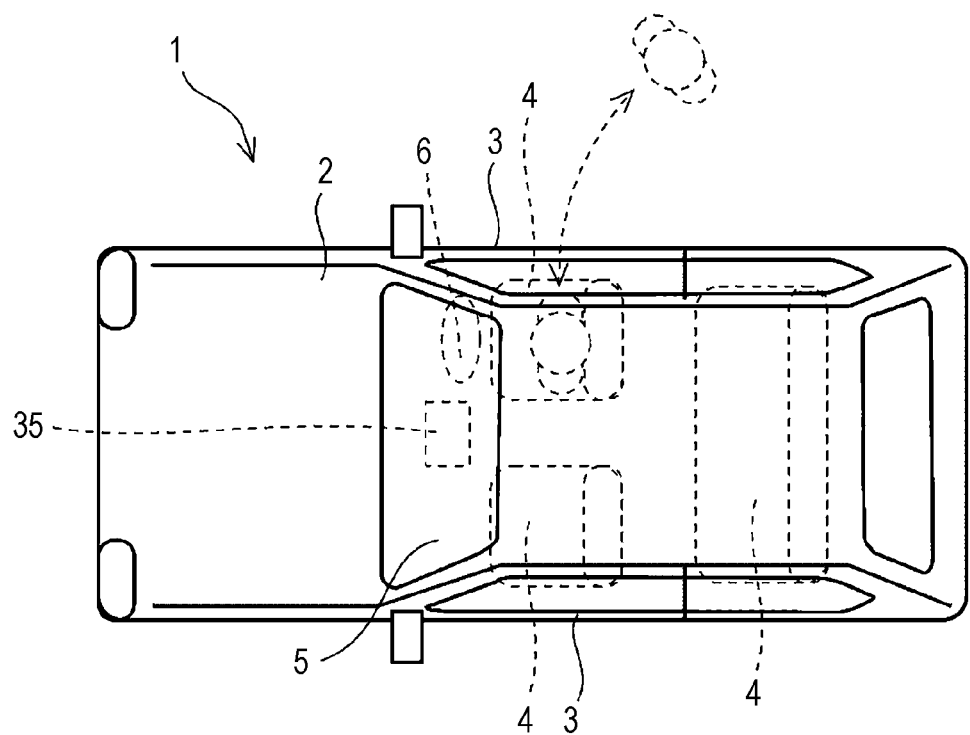
FIG. 1 is an explanatory view of an automobile to which an occupant monitoring device according to an example of the present invention is applied.

FIG. 1 is an explanatory view of an automobile 1 to which an occupant monitoring device according to an example of the present invention is applied.

The automobile 1 is an instance of a vehicle. As a power source for driving, the automobile 1 may use an internal-combustion engine, stored electric power of a battery, or a combination of the internal-combustion engine and the stored electric power.

The automobile 1 of FIG. 1 includes a vehicle body 2 in which a passenger compartment is formed, and doors 3 provided on the sides of the vehicle body 2.

An occupant such as a driver opens a door 3, goes into the passenger compartment, and sits down on a seat 4. On the front side of the seat 4 for the driver, operation members are disposed, the operation members including, for instance, a steering wheel 6 projecting backward from a dashboard 5, an ignition switch, an accelerator pedal, a brake pedal, a shift lever, and a parking lever.

The driver operates the operation members while seated on the seat 4. The automobile 1 runs, changes the direction, and stops according to an operation of the driver.

Also, an occupant such as a driver stops the automobile 1 by operating the ignition switch, then opens the door 3 to leave the passenger compartment.

Figure 2:
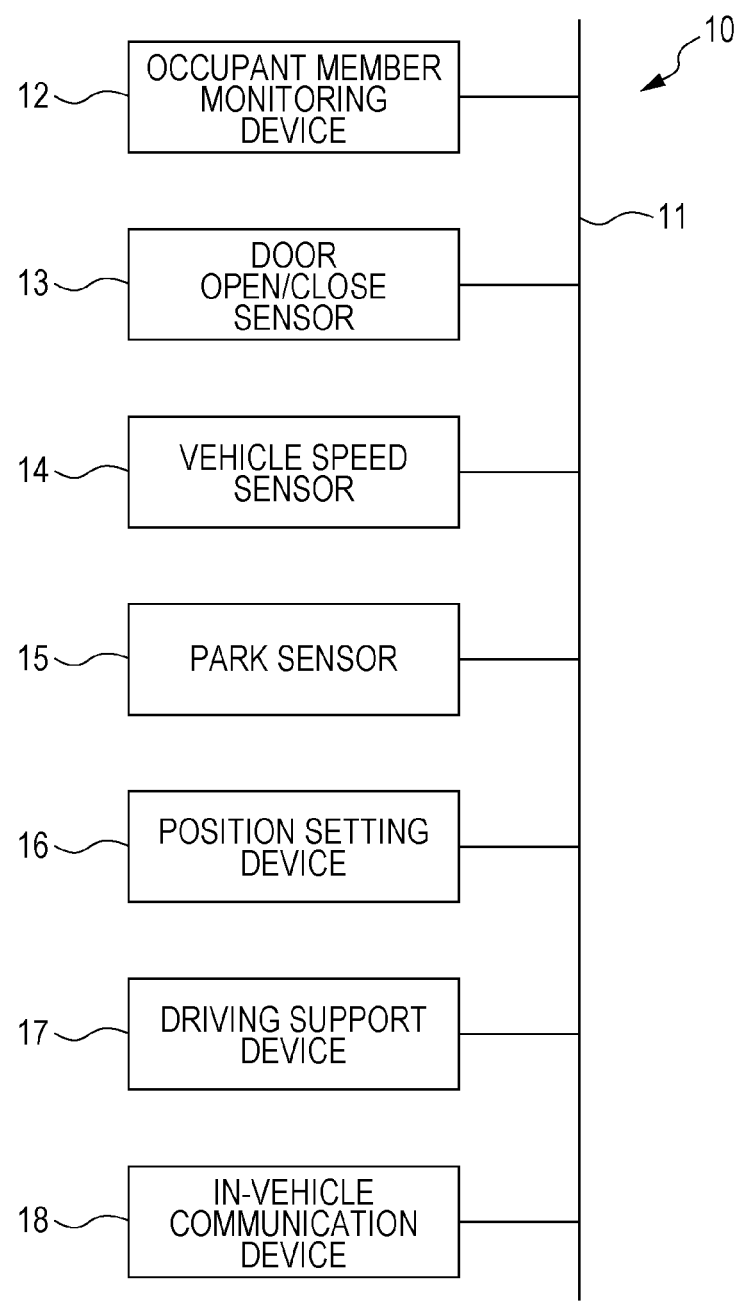
FIG. 2 is an explanatory diagram of an instance of an in-vehicle network system of the automobile of FIG. 1.

FIG. 2 is an explanatory diagram of an instance of an in-vehicle network system 10 of the automobile 1 of FIG. 1.

In the in-vehicle network system 10, multiple electronic devices capable of communicating with each other are connected via an in-vehicle network 11 to allow data communication between the electronic devices.

FIG. 2 illustrates an occupant monitoring device 12, a door open/close sensor 13, a vehicle speed sensor 14, a park sensor 15, a position setting device 16, a driving support device 17, and a vehicle exterior communication device 18 as the multiple electronic devices.

The in-vehicle network 11 may be, for instance, a wired communication network in conformity with the Controller Area Network (CAN), or the Local Interconnect Network (LIN). The in-vehicle network 11 may be a wireless communication network.

Also, after the occupants get off the vehicle, the in-vehicle network 11 may be in a sleep state in which communication is restricted. In this case, when a driver rides on the vehicle, the in-vehicle network 11 assumes a start state in which communication is possible. The in-vehicle network 11 assumes a start state from a sleep state based on detection of, for instance, a keyless entry device possessed by an occupant. The in-vehicle network 11 may include a network controller that autonomously switches between an ON state and an OFF state.

The occupant monitoring device 12 recognizes, for instance, an occupant who has entered the passenger compartment and has seated on the seat 4 for the driver, and monitors the recognized occupant for inattentive driving and/or drowsy driving. When inattentive driving and/or drowsy driving of the driver is detected, the occupant monitoring device 12 gives warning to the driver through sound. Thus, attention of the driver is focused on the driving of the automobile 1, and improved safety can be expected.

The door open/close sensor 13 detects opening of each door 3 of the automobile 1 in a closed state and closing of each door 3 in an open state.

The vehicle speed sensor 14 detects stopping and driving of the automobile 1. The vehicle speed sensor 14 may detect a running speed of the automobile 1.

The park sensor 15 detects a parking state in which the automobile 1 is maintained in a vehicle stop state. The parking state can be detected, for instance, by the operation of the shift lever to a parking position or pulling of the parking lever.

The position setting device 16 adjusts, for instance, the fore-and-aft and vertical position of the seat 4, and the angle of the backrest, the fore-and-aft and vertical position and the angle of the steering wheel 6, and the fore-and-aft and vertical positions and angles of various pedals. Also, setting data corresponding to an occupant who has sit on the seat 4 is recorded, and control is performed to adjust the positions and angles of the seat 4, the steering wheel 6, and the pedals based on the setting data. It is to be noted that the position setting device 16 may record setting data for the positions during automatic driving separately from setting data for the positions during manual driving, and may change any position according to a driving situation of the automobile 1.

The driving support device 17 controls the driving, stopping, and steering of the automobile 1 to support the driving operation of the automobile 1 by the driver. Also, the driving support device 17 may control the driving, stopping, and steering of the automobile 1 fully automatically.

The vehicle exterior communication device 18 performs bidirectional data communication with the vehicle exterior communication device 18 of each of other automobiles 1 and/or communication facilities installed on the ground using a public radio communication network or a commercial radio communication network, for instance. Thus, the automobile 1 can obtain information on traffic information, the running states of other automobiles 1 in the surrounding, and a traffic situation around the automobile 1. In addition, the vehicle exterior communication device 18 can transmit information on the driving state of the automobile 1, such as an automatic driving state, for instance.

These electronic devices mutually transmit and receive data via the in-vehicle network 11. Thus, the occupant monitoring device 12 can obtain, for instance, information necessary for its control, and can provide information necessary for the position setting device 16 and the driving support device 17.

Meanwhile, some occupants may think that warning given by the occupant monitoring device 12 is unnecessary or may feel that the warning is annoying.

Thus, it is desirable that start or stop of the occupant monitoring device 12 can be set by an operation of an occupant.

However, even when the turned off occupant monitoring device 12 is turned on, the occupant monitoring device 12 cannot start monitoring each occupant riding in the automobile 1 unless each occupant is recognized.

When an occupant such as a driver is replaced during travel of the automobile 1, a replacing occupant has to wait until the occupant monitoring device 12 finishes recognizing the occupant.

If the automobile travel is resumed before the occupant monitoring device 12 finishes properly recognizing each occupant, the occupant monitoring device 12 may monitor an occupant different from an actual driver for inattentive driving and/or drowsy driving with the occupant recognized as the driver. It is not preferable that monitoring of occupants be allowed in such an inconsistent state.

It is desirable that the occupant monitoring device 12 be preferably turned on or off in the automobile 1.

Figure 3:
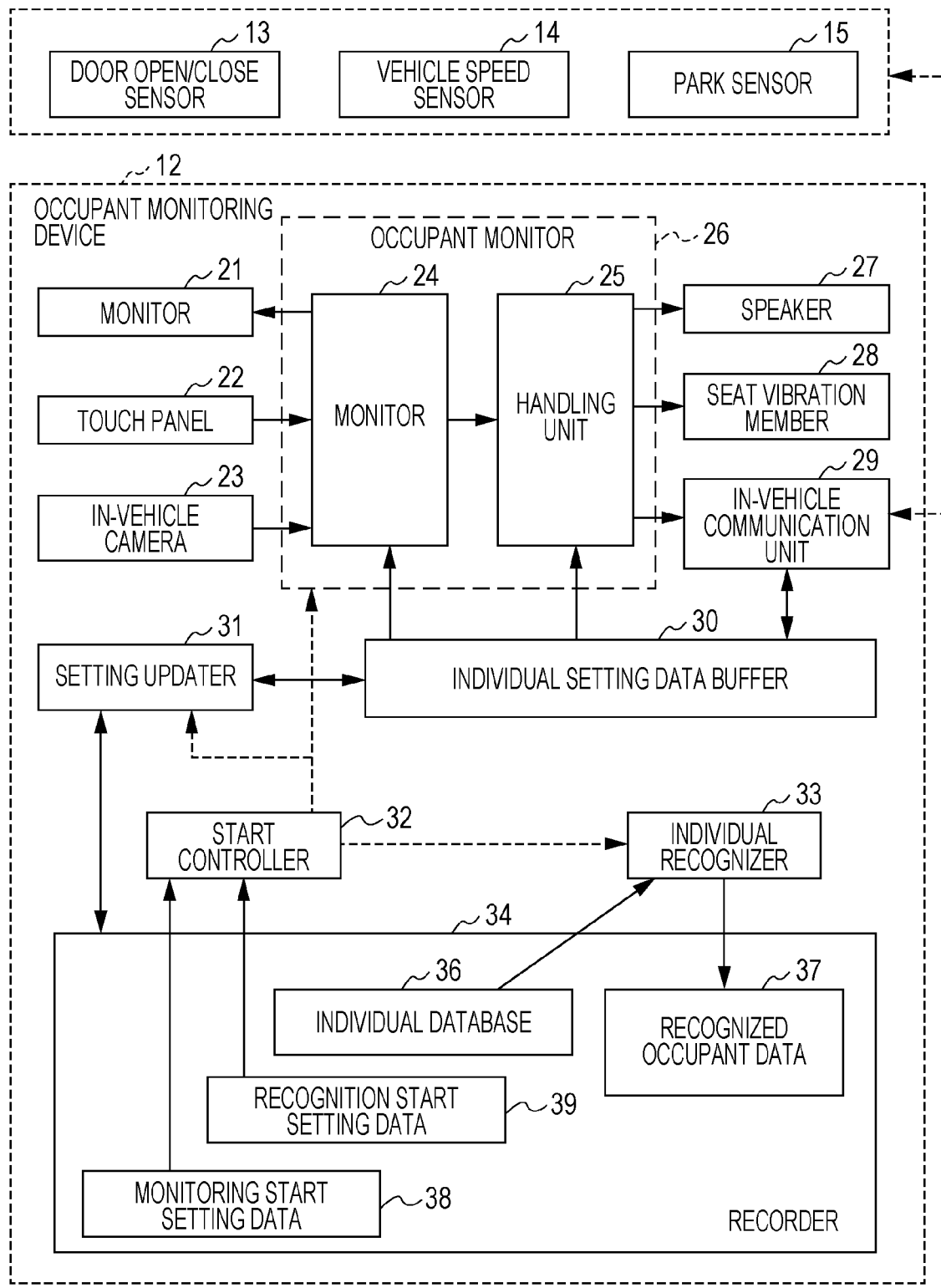
FIG. 3 is an explanatory diagram of the occupant monitoring device according to the example of the present invention.

FIG. 3 is an explanatory diagram of the occupant monitoring device 12 according to the example of the present invention.

FIG. 3 illustrates the door open/close sensor 13, the vehicle speed sensor 14, and the park sensor 15 along with the occupant monitoring device 12, and the sensors are capable of transmitting and receiving data to and from the occupant monitoring device 12 via the in-vehicle network 11. The door open/close sensor 13 transmits information on an open/close state of each door 3 to the occupant monitoring device 12. The vehicle speed sensor 14 transmits information on the speed of the automobile 1 to the occupant monitoring device 12. The park sensor 15 transmits information on whether or not the automobile 1 is in a parking state to the occupant monitoring device 12. An occupant monitoring system includes these sensors. These sensors may be provided as part of the occupant monitoring device 12.

The occupant monitoring device 12 of FIG. 3 includes a monitor 21, a touch panel 22, an in-vehicle camera 23, an occupant monitor 26 having a monitor 24 and a handling unit 25, a speaker 27, a seat vibration member 28, an in-vehicle communication unit 29, an individual setting data buffer 30, a setting updater 31, a start controller 32, an individual recognizer 33, and a recorder 34.

The speaker 27 and the seat vibration member 28 may be provided in the automobile 1 separately from the occupant monitoring device 12, and may be capable of transmitting and receiving data to and from the occupant monitoring device 12 via the in-vehicle network 11.

It is to be noted that the occupant monitor 26, the setting updater 31, the start controller 32, and the individual recognizer 33 may be implemented in the occupant monitoring device 12 by a microcomputer device, such as an electric control unit (ECU) of the occupant monitoring device 12, executing a program. Also, the individual setting data buffer 30, the recorder 34, and the in-vehicle communication unit 29 may be provided in the occupant monitoring device 12 with incorporated in a microcomputer device. The program may be recorded on the recorder 34.

The monitor 21 is a display member such as a liquid crystal device. The monitor 21 displays, for instance, an operation screen, a monitoring screen, a warning screen to provide information to a user.

The touch panel 22 is a member operated by a user. The touch panel 22 may be provided overlapping with the monitor 21. The user interface of the occupant monitoring device 12 is formed by the monitor 21 and the touch panel 22.

The in-vehicle camera 23 is a member that captures an image in the passenger compartment. The in-vehicle camera 23 may capture the head of the driver, or may capture the passenger compartment in 360 degree overall directions.

As illustrated in FIG. 1, a main body 35 of the occupant monitoring device 12 is disposed at a central portion of the dashboard 5, thus the driver and an occupant sitting on the front passenger seat can view the display screen of the monitor 21 and operate the touch panel 22. Also, the in-vehicle camera 23 can capture the head of the driver from the front side.

The speaker 27 is a member that outputs voice into the passenger compartment. The speaker 27 may be connected to the main body 35 of the occupant monitoring device 12 via an audio cable, and may be provided in each door 3.

The seat vibration member 28 is a member that vibrates. The seat vibration member 28 is connected to the main body 35 of the occupant monitoring device 12 via a signal cable, and is provided in the seat 4 for the driver. It is to be noted that instead of the seat vibration member 28, a vibration member built in the steering wheel 6 may be provided.

The in-vehicle communication unit 29 is connected to the in-vehicle network 11. The in-vehicle communication unit 29 receives information necessary for the occupant monitoring device 12 as needed or periodically. In addition, the in-vehicle communication unit 29 transmits information on the occupant monitoring device 12 as needed or periodically. The in-vehicle communication unit 29 receives, for instance, information on the open/close state of each door 3, information on the speed of the automobile 1, and information on whether or not the automobile 1 is in a parking state.

The recorder 34 is a member that holds recorded data even when no power is supplied. The recorder 34 may be, for instance, a non-volatile memory. The recorder 34 holds, for instance, individual database 36, recognized occupant data 37, monitoring start setting data 38, and recognition start setting data 39.

FIG. 4 is an explanatory table of correspondence relationships between setting values of monitoring start setting data 38, setting values of recognition start setting data 39 of FIG. 3, and turn on/off states of the occupant monitoring device 12.

As illustrated in FIG. 4, when the monitoring start setting data 38 (occupant monitoring) has a setting value of ON, inattentive driving detection function and drowsy driving detection function are enabled. The start controller 32 starts the occupant monitor 26. The occupant monitor 26 assumes a state which allows monitoring to be started.

On the other hand, when the monitoring start setting data 38 (occupant monitoring) has a setting value of OFF, inattentive driving detection function and drowsy driving detection function are disabled. The start controller 32 turns off the occupant monitor 26. The occupant monitor 26 ends monitoring.

When the recognition start setting data 39 (individual recognition) has a setting value of ON, individual recognition function is enabled. The start controller 32 starts the individual recognizer 33. The individual recognizer 33 assumes a state which allows authentication to be started.

On the other hand, when the recognition start setting data 39 has a setting value (individual recognition) of OFF, individual recognition function is disabled. The start controller 32 stops the individual recognizer 33. The individual recognizer 33 ends the authentication.

The start controller 32 individually controls start and stop of the occupant monitor 26 and the individual recognizer 33 according to an ON/OFF state of the in-vehicle network 11.

When the in-vehicle network 11 assumes an ON state, the start controller 32 individually starts the occupant monitor 26 and the individual recognizer 33 with the setting values of the monitoring start setting data 38 and the setting values of the recognition start setting data 39 at that point.

When the in-vehicle network 11 assumes an OFF state, the start controller 32 stops along with the occupant monitor 26 and the individual recognizer 33.

It is to be noted that the start controller 32 may individually control the occupant monitor 26 and the individual recognizer 33 according to an ON/OFF state of an ignition switch for starting the function of the automobile 1.

In this manner, in a setting state in which the occupant monitor 26 is stopped, the start controller 32 can start the individual recognizer 33 based on settings for starting the individual recognizer 33.

The occupant monitor 26 capable of starting to monitor performs monitoring processing basically during driving of the automobile 1 in order to secure the safety during the driving.

Also, when the automobile 1 is stopped and the necessity for occupant monitoring is low, the individual recognizer 33 performs individual recognition processing as needed.

FIG. 5 is an explanatory table for the data structure of the individual database 36 of FIG. 3.

In FIG. 5, the record, appearing in each row, of the individual database 36 corresponds to an occupant riding in the automobile 1. The record has, for instance, an individual ID, face data, a setting value to start monitoring, a setting value to start recognition, and individual setting data.

The individual ID is an identification number issued for an occupant so that no overlap occurs between the identification numbers of registered occupants.

The face data is data obtained by capturing the faces of registered occupants.

The individual setting data is registered setting data for the automobile 1 for each registered occupant. The individual setting data has, for instance, a setting value of ON/OFF of the speaker 27, a setting value of ON/OFF of the vibration member, and a setting value of an occupant position such as the seat 4 and the steering wheel 6.

The individual setting data buffer 30 stores the individual IDs and the setting data of recognized occupants. The setting data is utilized by the occupant monitor 26. Part of the individual IDs or the setting data is transmitted to other electronic devices by the in-vehicle communication unit 29.

The other electronic devices perform various types of individual setting control based on the received individual IDs or setting data. For instance, the position setting device 16 adjusts the fore-and-aft and vertical position of the seat 4 and the angle of the backrest based on the received setting data or setting data recorded in the position setting device 16, corresponding to the received individual IDs.

When the setting value of the recognition start setting data 39 is ON setting which allows authentication to be started, the individual recognizer 33 performs individual recognition processing to recognize the occupants riding in the automobile 1.

Although the details of the individual recognition processing will be described later, the individual recognizer 33 compares the images of the faces of the occupants captured by the in-vehicle camera 23 with multiple pieces of face data registered in the individual database 36.

When face data is obtained in which a predetermined matching value is available, the individual recognizer 33 updates the recognized occupant data 37 with an individual ID which is registered in the individual database 36 and corresponds to the face data with a highest matching value.

Thus, the individual IDs corresponding to the occupants riding in the automobile 1, are registered in the recognized occupant data 37.

The setting updater 31 updates the monitoring start setting data 38 and the recognition start setting data 39 based on an operation of the touch panel 22.

The setting updater 31 adds a record to, deletes a record from, or updates the records of the individual database 36 based on an operation of the touch panel 22.

The setting updater 31 updates a setting value of the individual setting data buffer 30 based on an operation of the touch panel 22.

When the occupant monitor 26 assumes a state which allows monitoring to be started or when the recognized occupant data 37 is updated during monitoring, the setting updater 31 reads records in the individual database 36, which correspond to the individual IDs of the recognized occupant data 37, and sets these records to the monitoring start setting data 38, the recognition start setting data 39, and the individual setting data buffer 30.

Thus, in a setting state in which the occupant monitor 26 is started, the setting updater 31 updates the setting data of the individual setting data buffer 30 according to a result of authentication of an occupant performed by the individual recognizer 33, and in a setting state in which the occupant monitor 26 is stopped, the setting updater 31 does not update the setting data of the individual setting data buffer 30. Also, the individual setting data buffer 30 records the setting data corresponding to the occupants recognized by the individual recognizer 33.

When the occupant monitor 26 ends monitoring, the setting updater 31 updates the individual database 36 with the setting values of the monitoring start setting data 38, the recognition start setting data 39, and the individual setting data buffer 30.

When an OFF operation of the ignition switch of the automobile 1 is performed, the occupant monitor 26 updates the individual database 36 with the data at that point. Save processing for the buffer is performed.

It is to be noted that the occupant monitor 26 may update the individual database 36 with the setting values of the monitoring start setting data 38, the recognition start setting data 39, and the individual setting data buffer 30 as needed when appropriate. By the update, all the setting values of the individual database 36 may be the updated or part of the setting values of the individual database 36 may be the updated. For instance, the occupant monitor 26 may register setting values to be used by the occupant monitoring device 12 at the same time when an individual ID is registered in the individual database 36, and at the time of a subsequent ignition off operation, may register setting values of other devices, such as a temperature of the air-conditioner (not illustrated) of the automobile 1, in the individual database 36.

The occupant monitor 26 has the monitor 24 and the handling unit 25.

When the setting value of the monitoring start setting data 38 is ON setting which allows authentication to be started, the monitor 24 performs monitoring processing to monitor the occupants riding in the automobile 1 according to a result of recognition of the occupants by the individual recognizer 33.

In the monitoring processing, the monitor 24 determines whether or not the image of the face of an occupant captured by the in-vehicle camera 23 is in a state corresponding to a predetermined state of a target to be monitored, based on the face data registered in the individual database 36 corresponding to the individual ID registered in the recognized occupant data 37.

For instance, when an occupant is to be monitored for inattentive driving, it is determined whether or not a state, in which the orientation of the face in the captured image deviates from the forward traveling direction, continues for a predetermined time or longer.

Also, when an occupant is to be monitored for drowsy driving, it is determined whether or not a state has occurred, in which the eyes in the captured image are closed a predetermined number of times or greater or for a predetermined time or longer.

When an individual ID is not registered in the recognized occupant data 37, the monitor 24 may determine whether or not the image of the face of an occupant captured by the in-vehicle camera 23 is in a state corresponding to a predetermined state of a target to be monitored, based on generalized standard face data.

When it is determined by the monitor 24 that a warning state has occurred, the handling unit 25 performs warning processing.

In the warning processing, the handling unit 25 checks the setting values of the individual setting data buffer 30. When a setting value for turning on the speaker 27 is present, the handling unit 25 outputs warning sound from the speaker 27 for a certain period. When a setting value for turning on the vibration member is present, the handling unit 25 vibrates the seat vibration member 28 for a certain period. In addition, the handling unit 25 checks the setting values of the individual setting data buffer 30, and when a setting value for turning on the display is present, the handling unit 25 displays warning on the monitor 21.

In this manner, the occupant monitor 26 of the occupant monitoring device 12 monitors the occupants riding in the automobile 1 according to a result of recognition of the occupants by the individual recognizer 33, and can output warning through display or sound as needed.

In a setting state in which the occupant monitor 26 is started and in a setting state in which the occupant monitor 26 is stopped, the in-vehicle communication unit 29 transmits the setting data of recognized occupants, set in the individual setting data buffer 30 to other electronic devices provided in the automobile 1.

The in-vehicle communication unit 29 may periodically transmit the setting data to other electronic devices in a repetitive manner.

Figure 6:
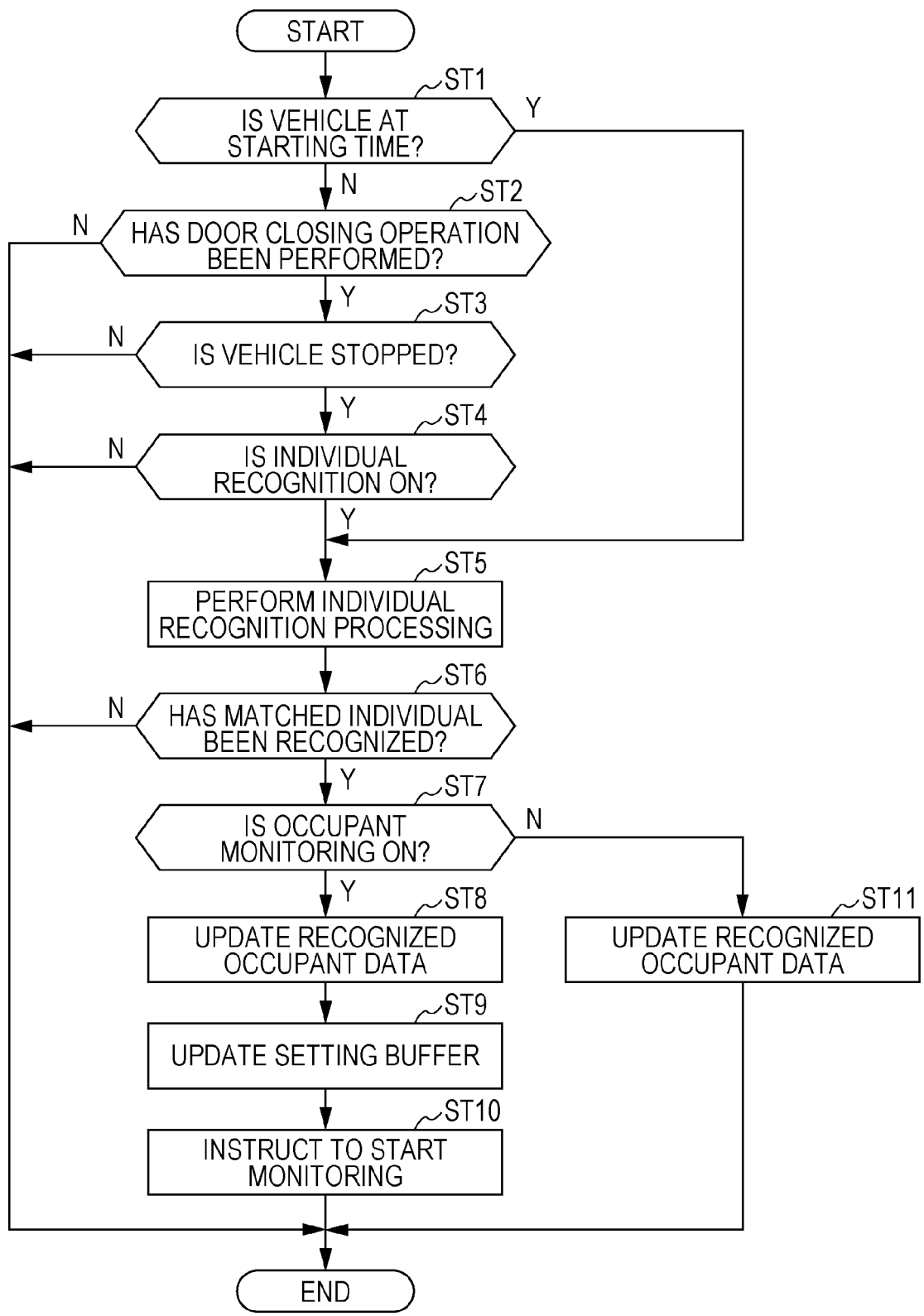
FIG. 6 is a flowchart illustrating the flow of occupant recognition processing performed by the occupant monitoring device of FIG. 2.

FIG. 6 is a flowchart illustrating the flow of occupant recognition processing performed by the occupant monitoring device 12 of FIG. 2.

The start controller 32 of the occupant monitoring device 12 periodically performs the processing of FIG. 6 in a repetitive manner.

In the occupant recognition processing of FIG. 6, the start controller 32 first determines whether or not it is the starting time of the automobile 1 (step ST1). The start controller 32 may determine whether or not it is the starting time of the automobile 1, for instance, based on whether the lapse of time since an ON operation of the ignition switch of the automobile 1 is within a predetermined period. When it is the starting time of the automobile 1, the individual recognizer 33 performs the individual recognition processing in step ST5 regardless of starting or stopping of the occupant monitor 26.

When a predetermined period has elapsed since start of the automobile 1, the start controller 32 determines that it is not the starting time, and determines whether or not a close operation is performed on any door 3 (step ST2). The individual recognizer 33 may determine whether or not a close operation is performed on any door 3, based on a detection value of the door open/close sensor 13, received by the in-vehicle communication unit 29, for instance. When an occupant rides on the automobile 1, the occupant opens a door 3, and closes the door 3 with seated on the seat 4. Riding of an occupant in the automobile 1 can be detected by a detection value of the door open/close sensor 13. The start controller 32 may determine that an open operation is performed on the door 3, and open and close operations are performed on the door 3. When a close operation is not performed on any door 3, the start controller 32 ends the processing of FIG. 6.

When a close operation is performed on any door 3, the start controller 32 determines whether or not the automobile 1 is stopped (step ST3). The start controller 32 may determine that the automobile 1 is stopped based on that a detection speed of the vehicle speed sensor 14, received by the in-vehicle communication unit 29, is 0 kilometers per hour. When the automobile 1 is not stopping, the start controller 32 ends the processing of FIG. 6.

When the automobile 1 is stopped, the start controller 32 determines whether or not the setting of the individual recognition is ON based on the recognition start setting data 39 (step ST4). When the setting of the individual recognition is not ON, the start controller 32 ends the processing of FIG. 6.

When the setting of the individual recognition is ON or the current time is determined to be the starting time in step ST1, the start controller 32 instructs the individual recognizer 33 to perform individual recognition processing (step ST5). The individual recognizer 33 compares the images of the faces of the occupants captured by the in-vehicle camera 23 with multiple pieces of face data registered in the individual database 36, and performs processing to recognize and identify the individuals riding on the automobile 1.

Subsequently, the individual recognizer 33 determines whether or not matching individual has been recognized (step ST6). When a matching result is not obtained, the individual recognizer 33 ends the individual recognition processing. In this case, the recognized occupant data 37 is not updated.

When a matching result is obtained, the individual recognizer 33 determines whether or not the setting of occupant monitoring is ON based on the monitoring start setting data 38 (step ST7).

When the setting of occupant monitoring is ON, the individual recognizer 33 updates the recognized occupant data 37 with a registered individual ID corresponding to face data determined to be matched (step ST8). Subsequently, the setting updater 31 reads setting data, from the individual database 36, which corresponds to an individual ID registered in the recognized occupant data 37, and updates the individual setting data buffer 30 (step ST9). Thus, the setting data of a recognized occupant is registered in the individual setting data buffer 30. In addition, the setting updater 31 instructs the occupant monitor 26 to perform occupant monitoring (step ST10). The occupant monitor 26 can start the occupant monitoring based on the setting data of the updated individual setting data buffer 30.

When the setting of occupant monitoring is OFF, the individual recognizer 33 updates the recognized occupant data 37 with a registered individual ID corresponding to face data determined to be matched (step ST11). In this case, the setting updater 31 does not update the individual setting data buffer 30. Therefore, the occupant monitor 26 starts or continues the occupant monitoring based on the setting data previously registered in the individual setting data buffer 30.

Figure 7:
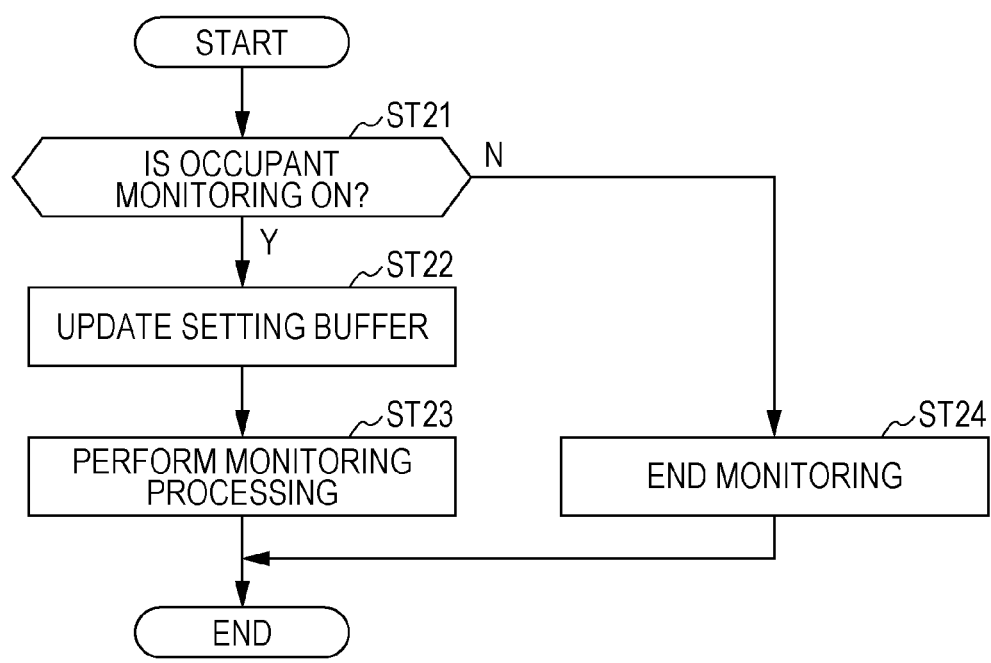
FIG. 7 is a flowchart illustrating the flow of monitoring start processing performed by the occupant monitoring device of FIG. 2.

FIG. 7 is a flowchart illustrating the flow of monitoring start processing performed by the occupant monitoring device 12 of FIG. 2.

The occupant monitor 26 of the occupant monitoring device 12 periodically performs the processing of FIG. 7 in a repetitive manner.

In FIG. 7, the occupant monitor 26 determines whether or not the setting of occupant monitoring is ON based on the monitoring start setting data 38 (step ST21).

When the setting of occupant monitoring is ON, the setting updater 31 reads setting data from the individual database 36 based on the instruction of the occupant monitor 26, the setting data corresponding to an individual ID registered in the recognized occupant data 37, and updates the individual setting data buffer 30 (step ST22). Thus, the setting data of the most recently recognized occupant is registered in the individual setting data buffer 30. Subsequently, the occupant monitor 26 reads setting data used for control of monitoring from the individual setting data buffer 30, and performs monitoring according to the setting (step ST23).

When the setting of occupant monitoring is OFF, the occupant monitor 26 performs processing to end the monitoring (step ST24). The setting updater 31 reads the setting data of the individual setting data buffer 30 based on the instruction of the occupant monitor 26, and updates corresponding setting data in the individual database 36. Consequently, the most recent setting data of the occupants is always recorded in the individual database 36.

Figure 8:
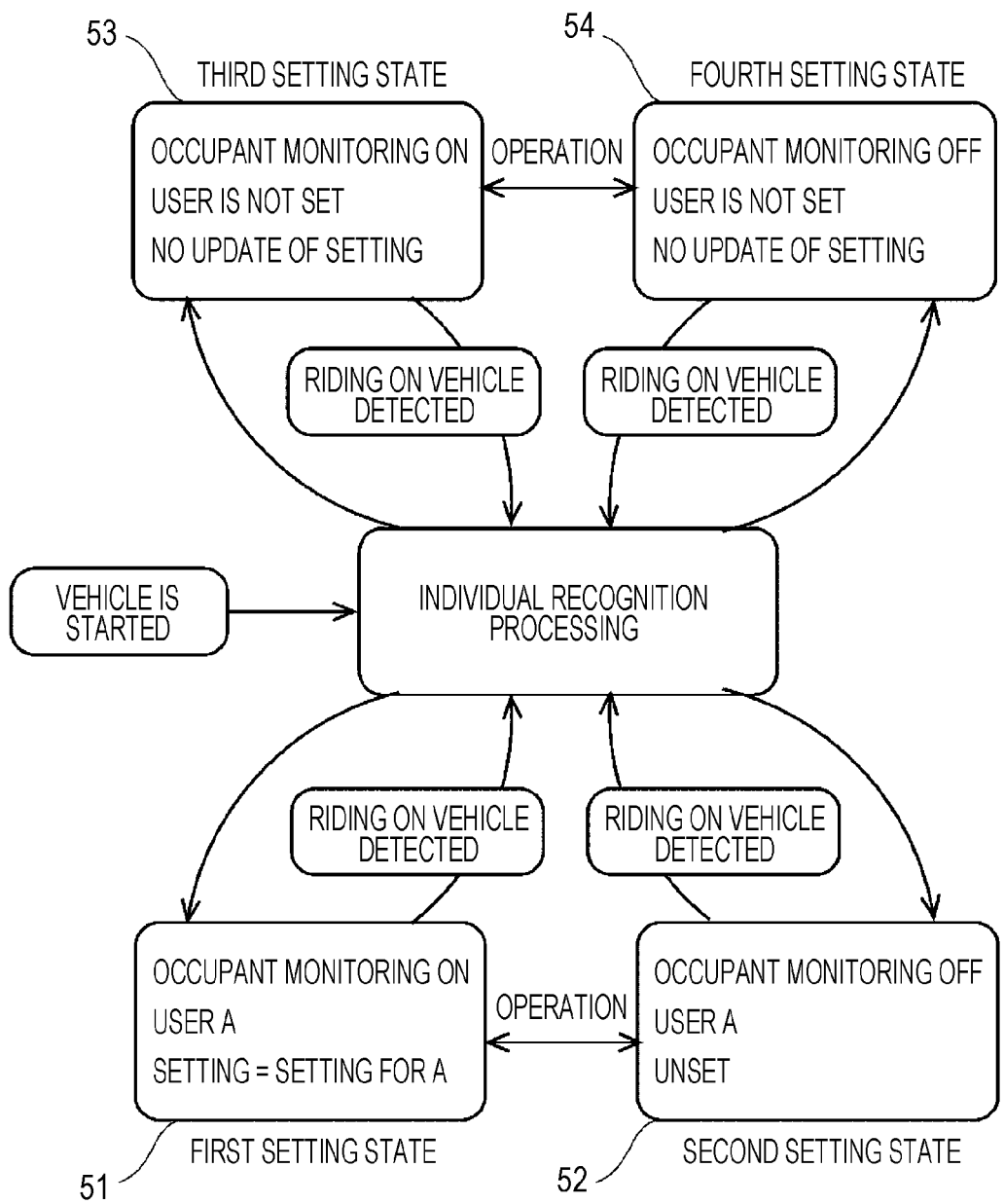
FIG. 8 is an explanatory diagram of transition of setting states in the occupant monitoring device of FIG. 2.

FIG. 8 is an explanatory diagram of transition of setting states in the occupant monitoring device 12 of FIG. 2. In FIG. 8, it is assumed that the setting of individual recognition is ON.

As illustrated in FIG. 8, when the automobile 1 is started, individual recognition processing may be performed. Each occupant riding in the automobile 1 is recognized by the individual recognition processing.

When a recognized occupant is registered in the individual database 36, the setting state of the occupant monitoring device 12 becomes a first setting state 51 or a second setting state 52.

The first setting state 51 is for the situation where the setting of occupant monitoring is ON. In this case, registered user A is authenticated, and the setting value of user A is set to the individual setting data buffer 30 for occupant monitoring. In this case, the occupant monitoring device 12 identifies each occupant riding in the automobile 1, and monitors the occupant.

The second setting state 52 is for the situation where the setting of occupant monitoring is OFF. In this case, user A is authenticated, but the setting value of user A is not set to the individual setting data buffer 30. Subsequently, the first setting state 51 is assumed, and the setting value of user A is set. However, when an operation is performed subsequently to set occupant monitoring OFF and transition is made from the first setting state 51, the setting value of user A is set to the individual setting data buffer 30.

When riding in the automobile 1 is detected, each occupant is authenticated again in a new riding state by individual recognition processing.

For instance, when user B registered in the individual database 36 is recognized, the setting state of the occupant monitoring device 12 becomes the first setting state 51 or the second setting state 52 for user B.

However, when user C unregistered in the individual database 36 is recognized, the setting state of the occupant monitoring device 12 becomes a third setting state 53 or a fourth setting state 54.

The third setting state 53 is for the situation where the setting of occupant monitoring is ON. In this case, since user C is unregistered, no setting is made for the user, and the individual setting data buffer 30 is not updated, either. Setting data not associated with user C remains registered in the individual setting data buffer 30. In this case, the occupant monitoring device 12 monitors each occupant riding in the automobile 1 with the occupant unidentified. Subsequently, when an operation is performed to set occupant monitoring OFF, the fourth setting state 54 is assumed.

The fourth setting state 54 is for the situation where the setting of occupant monitoring is OFF. Also in this case, no setting is made for the user, and the individual setting data buffer 30 is not updated, either. Subsequently, when an operation is performed to set occupant monitoring ON, the third setting state 53 is assumed.

In this manner, the occupant monitoring device 12 of the embodiment makes transition to a different setting state according to ON/OFF setting of occupant monitoring and a result of individual recognition.

As described above, in the embodiment, the individual recognizer 33 that recognizes each occupant riding in the automobile 1, and the occupant monitor 26 that monitors each occupant riding in the automobile 1 based on the setting of the occupant recognized by the individual recognizer 33 can be individually started or stopped. Thus, start or stop is individually set to the individual recognizer 33 and the occupant monitor 26, and the individual recognizer 33 and the occupant monitor 26 can be individually started or stopped.

In the embodiment, in the setting state in which the occupant monitor 26 is stopped, the individual recognizer 33 can be started based on the setting in which the individual recognizer 33 is started. Thus, in the setting state in which the occupant monitor 26 is stopped, each occupant riding in the automobile 1 can be recognized. When the occupant monitor 26 is started subsequently, the occupant monitor 26 can immediately and appropriately start monitoring of each occupant who has ridden in the automobile 1 while stopping and has been recognized without waiting for recognition by the individual recognizer 33. The occupant monitoring device 12 can be preferably started or stopped.

When a specific occupant is recognized by the individual recognizer 33, the occupant monitor 26 monitors the recognized occupant, and when a specific occupant is not recognized by the individual recognizer 33, the occupant monitor 26 can monitor each occupant riding in the automobile 1 with the occupant unidentified.

In contrast, for instance, if the entire occupant monitoring device 12 is overall controlled for starting and stopping based on one setting, even when the occupant monitoring device 12 is started, the occupant monitoring device 12 cannot start monitoring each occupant riding in the automobile 1 unless each occupant is recognized. Thus, it is not possible to cope with the problem specific to the automobile 1 in which riding on and riding off of an occupant is repeated as needed. When an occupant such as a driver is replaced during travel of the automobile 1, a replacing occupant has to wait until the occupant monitoring device 12 finishes recognizing himself or herself. When the automobile travel is resumed before the occupant monitoring device 12 recognizes each occupant, the occupant monitoring device 12 monitors an occupant different from an actual driver for inattentive driving and/or drowsy driving with the occupant recognized as the driver. It is not preferable to allow monitoring in such a situation.

In the embodiment, when riding of an occupant in the automobile 1 is detected, even in the setting state in which the occupant monitor 26 is stopped, the individual recognizer 33 is started. Thus, when an occupant rides in the automobile 1, the occupant riding in the automobile 1 can be recognized regardless of start or stop of the occupant monitor 26.

In the embodiment, when the automobile 1 is started, in the setting state in which the occupant monitor 26 is stopped, the individual recognizer 33 can be started. Thus, when the automobile 1 is started, each occupant riding in the automobile 1 can be recognized regardless of start or stop of the occupant monitor 26.

In the embodiment, during driving of the automobile 1, the occupant monitor 26 is started based on setting, and when the vehicle is stopped and the necessity for monitoring by the occupant monitor 26 is low, the individual recognizer 33 is started based on setting. Thus, the occupant monitor 26 is not prevented from monitoring during driving of the automobile 1, and each occupant can be identified by the individual recognizer 33.

In the embodiment, in the setting state in which the occupant monitor 26 is started, the individual setting data buffer 30, which records setting data to be utilized by the occupant monitor 26, is updated based on the most recent result of recognition of each occupant by the individual recognizer 33, and in the setting state in which the occupant monitor 26 is stopped, the individual setting data buffer 30 is not updated.

Thus, in the setting state in which the occupant monitor 26 is started, the monitor 24 updates the individual setting data buffer 30 based on recognition of change of occupants, and can monitor with the setting of updated occupants. Monitoring can be performed with consistency between the setting data and actual occupants.

Also, in the setting state in which the occupant monitor 26 is stopped, it is possible to avoid careless updating of the individual setting data buffer 30.

In particular, when the in-vehicle communication unit 29 transmits the setting data of recognized occupants in the individual setting data buffer 30 to other electronic devices provided in the automobile 1 in the setting state in which the occupant monitor 26 is started, if the buffer is updated in the setting state in which the occupant monitor 26 is stopped, inappropriate setting data may be transmitted to other electronic devices other than the occupant monitoring device 12. In the embodiment, transmission of such inappropriate setting data can be prevented.

Although the embodiment above is an example of a preferred embodiment of the present invention, the present invention is not limited to this, and various modification or changes may be made in the scope without departing from the spirit of the invention.

For instance, in the embodiment, riding of an occupant in the automobile 1 is detected by a close operation on a door 3. In addition, for instance, riding of an occupant in the automobile 1 may be detected by an open operation on a door 3. Also, riding of an occupant in the automobile 1 may be detected by occupant detection using a seat sensor for the seat 4.

In the embodiment, starting of the automobile 1 is detected by ON operation performed on the ignition switch of the automobile 1. In addition, for instance, starting of the automobile 1 may be detected by an operation of the accelerator pedal when the automobile 1 is stopped.

The invention claimed is:

1. An occupant monitoring device for a vehicle, the occupant monitoring device being mountable in the vehicle and configured to monitor one or more occupants riding in the vehicle, the occupant monitoring device comprising:
   a recognizer configured to recognize the one or more occupants riding in the vehicle;
   a monitor configured to monitor the one or more occupants riding in the vehicle according to a result of recognition of the one or more occupants by the recognizer;
   a start controller configured to individually start or stop the recognizer and the monitor,
   wherein the start controller starts the recognizer with the monitor in a stopped state;
   a buffer configured to record setting data corresponding to the one or more occupants recognized by the recognizer and being to be utilized by the monitor; and
   a setting updater configured to update the buffer according to a result of the recognition of the one or more occupants by the recognizer, wherein
   when in a start state of the monitor, the setting updater updates the buffer on a basis of a latest result of the recognition of the one or more occupants by the recognizer, and
   in a turn-off state of the monitor, the setting updater does not update the buffer.

2. The occupant monitoring device for the vehicle according to claim 1,
   wherein when a specific occupant is recognized by the recognizer, the monitor monitors the recognized specific occupant, and
   when the specific occupant is not recognized by the recognizer, the monitor monitors the one or more occupants with the specific occupant unidentified.

3. The occupant monitoring device for the vehicle according to claim 1,
   wherein when riding of an occupant in the vehicle is detected, the start controller starts the recognizer with the monitor in the stopped state.

4. The occupant monitoring device for the vehicle according to claim 2,
   wherein when riding of an occupant in the vehicle is detected, the start controller starts the recognizer with the monitor in the stopped state.

5. The occupant monitoring device for the vehicle according to claim 1,
   wherein when the vehicle is started, the start controller starts the recognizer with the monitor in the stopped state.

6. The occupant monitoring device for the vehicle according to claim 2,
   wherein when the vehicle is started, the start controller starts the recognizer with the monitor in the stopped state.

7. The occupant monitoring device for the vehicle according to claim 1,
   wherein the start controller individually starts or stops the recognizer and the monitor on a basis of settings of start or stop individually made for the recognizer and the monitor.

8. The occupant monitoring device for the vehicle according to claim 2,
   wherein the start controller individually starts or stops the recognizer and the monitor on a basis of settings of start or stop individually made for the recognizer and the monitor.

9. The occupant monitoring device for the vehicle according to claim 1,
   wherein the start controller
   starts the monitor while the vehicle is running, and
   starts the recognizer while the vehicle is stopped.

10. The occupant monitoring device for the vehicle according to claim 2,
    wherein the start controller
    starts the monitor while the vehicle is running, and
    starts the recognizer while the vehicle is stopped.

11. The occupant monitoring device for the vehicle according to claim 1, further comprising
    a communication unit configured to transmit the setting data, set in the buffer, of the recognized one or more occupants to another device provided in the vehicle.

12. The occupant monitoring device for the vehicle according to claim 2, further comprising
    a communication unit configured to transmit the setting data, set in the buffer, of the recognized one or more occupants to another device provided in the vehicle.

13. The occupant monitoring device for the vehicle according to claim 1, wherein the individual start or stop of the recognizer and the monitor is based on an ON/OFF sate of an in-vehicle network of the vehicle.

* * * * *